(12) United States Patent
Hajiaghaei (10) Patent No.: US 10,864,093 B2
(45) Date of Patent: Dec. 15, 2020

(54) SYSTEM AND A METHOD FOR ADJUSTING A PROSTHETIC LIMB

(71) Applicant: Behnam Hajiaghaei, Tehran (IR)

(72) Inventor: Behnam Hajiaghaei, Tehran (IR)

( * ) Notice: Subject to any disclaimer, the term of this patent is extended or adjusted under 35 U.S.C. 154(b) by 47 days.

(21) Appl. No.: 16/252,587

(22) Filed: Jan. 19, 2019

(65) Prior Publication Data

US 2019/0151120 A1 May 23, 2019

Related U.S. Application Data

(60) Provisional application No. 62/619,191, filed on Jan. 19, 2018.

(51) Int. Cl.
| | | |
|---|---|---|
| *A61F 2/78* | (2006.01) | |
| *A61F 2/80* | (2006.01) | |
| *A61F 2/76* | (2006.01) | |
| *A61F 2/60* | (2006.01) | |
| *A61F 2/68* | (2006.01) | |
| *A61F 2/50* | (2006.01) | |
| *A61F 2/74* | (2006.01) | |

(52) U.S. Cl.
CPC .............. *A61F 2/7843* (2013.01); *A61F 2/60* (2013.01); *A61F 2/68* (2013.01); *A61F 2/76* (2013.01); *A61F 2/78* (2013.01); *A61F 2002/501* (2013.01); *A61F 2002/5026* (2013.01); *A61F 2002/5027* (2013.01); *A61F 2002/5035* (2013.01); *A61F 2002/745* (2013.01); *A61F 2002/748* (2013.01); *A61F 2002/785* (2013.01)

(58) Field of Classification Search
CPC ...... A61F 2/78; A61F 2/80; A61F 2/60; A61F 2/7843; A61F 2002/745; A61F 2002/501
See application file for complete search history.

(56) References Cited

U.S. PATENT DOCUMENTS

| | | | | |
|---|---|---|---|---|
| 2,464,443 | A * | 3/1949 | Ganoe .................. | A61F 2/68 |
| | | | | 623/36 |
| 5,314,497 | A * | 5/1994 | Fay ..................... | A61F 2/7843 |
| | | | | 623/33 |
| 9,345,590 | B2 * | 5/2016 | Arabian ................ | A61F 2/68 |
| 10,426,639 | B2 * | 10/2019 | Erdmann ............... | A61F 2/68 |
| 10,517,746 | B2 * | 12/2019 | Bernhardt ............. | A61F 2/76 |
| 2003/0191539 | A1 * | 10/2003 | Caspers ................ | A61F 2/80 |
| | | | | 623/35 |

* cited by examiner

*Primary Examiner* — Bruce E Snow
(74) *Attorney, Agent, or Firm* — Bajwa IP Law Firm; Haris Zaheer Bajwa (57) ABSTRACT

A hydraulic system for adjusting a prosthetic limb. The hydraulic system may include an expandable pad mounted onto an interior surface of a socket of the prosthetic limb. The hydraulic system may further include a hydraulic cylinder and a plunger mechanism. The hydraulic cylinder may be filled with a hydraulic oil. The hydraulic system may be configured to expand the expandable pad by pumping the hydraulic oil from the hydraulic cylinder into the expandable pad responsive to a volume decrease of the residual limb being more than a threshold.

16 Claims, 9 Drawing Sheets

SYSTEM AND A METHOD FOR ADJUSTING A PROSTHETIC LIMB

CROSS-REFERENCE TO RELATED APPLICATION

This application claims the benefit of priority from U.S. Provisional Patent Application Ser. No. 62/619,191 filed on Jan. 19, 2018, and entitled "PROSTHETIC SOCKET WITH INTELLIGENTLY ADJUSTABLE INTERNAL VOLUME" which is incorporated herein by reference in its entirety.

TECHNICAL FIELD

The present disclosure generally relates to prosthetic systems, and particularly to a system and a method for adjusting a prosthetic limb.

BACKGROUND

A prosthetic device for an arm or leg is traditionally worn by inserting the residual limb into a rigid or semi-rigid socket. Traditional sockets are, generally, designed as a 360-degree container surrounding the entire residual limb. Sockets, generally, perform at least two broad functions. Firstly, traditional sockets are designed to allow comfortable weight bearing and prevent soft tissue damage as weight pressures are applied to the residual limb via the prosthetic socket. This is generally achieved with a combination of skeletal weight bearing and hydraulic lift created as the residual limb fluids are pressurized in the socket. Secondly, traditional sockets also function to stabilize the skeletal components of the residual limb so that the user is able to move the prosthesis in space and minimize relative motion between the socket and the residual limb.

A precise volumetric fit greatly aids both of these functions. Maintaining a proper amount of volumetric socket fit is challenging and often problematic due to the tendencies of the residual limb to change in volume and the soft tissue to displace under load. Residual limb volume change (RLVC) occurs due to many factors, including, but not limited to, edema, muscle atrophy, weight gain/loss, renal dialysis, salt and water intake, alcohol consumption, menses, and changes in wearing time and activity. Residual limbs also lose volume daily due to socket pressure and the pumping action of ambulation. Daily volume loss is generally replenished during non-wearing times, i.e., sleep, and is cyclical and greatly affected by activity.

As the residual limb loses volume, the hydrostatic weight bearing and skeletal control characteristics of the socket are compromised. This leads to painful, limiting, and/or injurious increases in socket pressure as well as energy wasting and destabilizing excessive motion between the socket and skeletal segments of the residual limb. As the user attempts to control the prosthesis in space by employing their proximal musculature, relative motion between the residual limb and prosthesis may cause forces which accelerate and impact the residual limb. These forces can be compressive, or cause strain or shear, which in turn increases localized pressure and/or tension on the residual limb. This commonly results in pain and injury, as well as increased energy use and premature fatigue. As a result, traditional sockets tend not to function well when changes in the residual limb's volume, shape, or size occur. This is a common occurrence and has not been addressed effectively.

Additionally, residual limbs are often bulbous in shape with the distal dimensions larger than those more proximal. This shape can cause difficulty in donning the socket because the socket pushes past the larger distal dimension to be secured to the smaller proximal socket dimension. There is, therefore, a need for a system and a method for adjusting a prosthetic limb socket such that the socket maintains a proper volumetric fit despite significant volume changes and reduces unwanted relative motion between the residual limb and the prosthesis.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one or more exemplary embodiments, the present disclosure describes an exemplary hydraulic system for adjusting a prosthetic limb. In an exemplary embodiment, the exemplary hydraulic system may include an expandable pad, a hydraulic cylinder, and a plunger mechanism. In an exemplary embodiment, the expandable pad may be mounted onto an interior surface of a socket of the prosthetic limb.

In an exemplary embodiment, the hydraulic cylinder may be filled with a hydraulic oil. In an exemplary embodiment, the plunger mechanism may be disposed between the hydraulic cylinder and the expandable pad. In an exemplary embodiment, the plunger mechanism may be configured to control fluid communication between the hydraulic cylinder and the expandable pad.

In an exemplary embodiment, the hydraulic system may be configured to expand the expandable pad by pumping the hydraulic oil from the hydraulic cylinder into the expandable pad responsive to a volume decrease of the residual limb being more than a threshold.

In an exemplary embodiment, the plunger mechanism may be configured to prevent fluid communication between the hydraulic cylinder and the expandable pad responsive to the volume decrease of the residual limb being less than the threshold. In an exemplary embodiment, the plunger mechanism may be further configured to allow fluid communication between the hydraulic cylinder and the expandable pad responsive to the volume decrease of the residual limb being equal to or more than the threshold. In an exemplary embodiment, the threshold may be in a range between 5% and 30% of an initial volume of the residual limb.

In an exemplary embodiment, the hydraulic system may further include a first hydraulic hose and a second hydraulic hose. In an exemplary embodiment, the first hydraulic hose may be configured to provide fluid communication between the plunger mechanism and the hydraulic cylinder. In an exemplary embodiment, the second hydraulic hose may be configured to provide fluid communication between the plunger mechanism and the expandable pad.

In an exemplary embodiment, the plunger mechanism may include a plunger rod and a plunger head. In an exemplary embodiment, the plunger rod may be disposed between the first hydraulic hose and the second hydraulic hose. In an exemplary embodiment, the plunger rod may be configured to prevent fluid communication between the hydraulic cylinder and the expandable pad. In an exemplary embodiment, the plunger rod may include a horizontal thorough hole. In an exemplary embodiment, the plunger head may be mounted onto the plunger rod.

In an exemplary embodiment, the plunger mechanism may be configured to allow fluid communication between the hydraulic cylinder and the expandable pad by aligning the horizontal thorough hole with the first the horizontal thorough hole with the first hydraulic hose and the second hydraulic hose responsive to the plunger head being tapped.

In an exemplary embodiment, the hydraulic cylinder may further include an outlet valve disposed between the hydraulic cylinder and the first hydraulic hose. In an exemplary embodiment, the outlet valve may be configured to allow fluid communication between the hydraulic cylinder and the first hydraulic hose responsive to the outlet valve being triggered. In an exemplary embodiment, the outlet valve may be connected to the socket. In an exemplary embodiment, the socket may be configured to trigger the outlet valve responsive to the socket pushed by the residual limb.

In an exemplary embodiment, the socket may include a residual limb opening, a cup-shaped interior surface, and a brim. In an exemplary embodiment, the residual limb opening may be positioned at a top end of the socket. In an exemplary embodiment, the cup-shaped interior surface may be shaped to receive the residual limb of the amputee.

In an exemplary embodiment, the expandable pad may be mounted onto the cup-shaped interior surface of the socket. In an exemplary embodiment, the expandable pad may be configured to grip the residual limb responsive to the expandable pad being expanded. In an exemplary embodiment, the brim may define a bottom open end. In an exemplary embodiment, the brim may be positioned in an adjustable distance above the plunger head.

In an exemplary embodiment, the cup-shaped interior surface may be configured to allow the residual limb slip down inside the socket responsive to the volume decrease of the residual limb more than the threshold. In an exemplary embodiment, the plunger head may be configured to be tapped by the slipped residual limb.

According to one or more exemplary embodiments, the present disclosure also describes an exemplary method for adjusting a prosthetic limb. In an exemplary embodiment, the method may include receiving a residual limb of an amputee in a socket of the prosthetic limb. In an exemplary embodiment, the prosthetic limb may include a hydraulic system. In an exemplary embodiment, the hydraulic system may include an expandable pad mounted onto an interior surface of the socket of the prosthetic limb.

In an exemplary embodiment, the hydraulic system may further include a hydraulic cylinder filled with hydraulic oil. In an exemplary embodiment, the hydraulic system may include a plunger mechanism disposed between the hydraulic cylinder and the expandable pad.

In an exemplary embodiment, the method may further include adjusting the expandable pad by controlling fluid communication between the hydraulic cylinder and the expandable pad utilizing the hydraulic system.

In an exemplary embodiment, adjusting the expandable pad by controlling fluid communication between the hydraulic cylinder and the expandable pad may include expanding the expandable pad by pumping the hydraulic oil from the hydraulic cylinder into the expandable pad responsive to an amount of volume decrease of the residual limb being more than a threshold.

In an exemplary embodiment, pumping the hydraulic oil from the hydraulic cylinder into the expandable pad may include allowing fluid communication between the hydraulic cylinder and the expandable pad responsive to the volume decrease of the residual limb being equal to or more than the threshold.

In an exemplary embodiment, allowing fluid communication between the hydraulic cylinder and the expandable pad may include allowing fluid communication between the hydraulic cylinder and the expandable pad utilizing a plunger mechanism.

In an exemplary embodiment, the plunger mechanism may include a plunger rod disposed between the hydraulic cylinder and the expandable pad. In an exemplary embodiment, the plunger rod may be connected to the hydraulic cylinder through a first hydraulic hose. In an exemplary embodiment, the plunger rod may be also connected to the expandable pad through a second hydraulic hose. In an exemplary embodiment, the plunger rod may include a horizontal thorough hole. In an exemplary embodiment, the plunger mechanism may further include a plunger head mounted onto the plunger rod.

In an exemplary embodiment, the first hydraulic hose may be connected to the plunger rod through a first opening. Similarly, in an exemplary embodiment, the second hydraulic hose may be connected to the plunger rod through a second opening.

In an exemplary embodiment, allowing fluid communication between the hydraulic cylinder and the expandable pad may include aligning the horizontal thorough hole with the first opening and the second opening through pushing down the plunger rod.

In an exemplary embodiment, expanding the expandable pad by pumping the hydraulic oil from the hydraulic cylinder into the expandable pad may include filling the first hydraulic hose with the hydraulic oil by pumping the hydraulic oil from the hydraulic cylinder into the second hydraulic hose. In an exemplary embodiment, expanding the expandable pad by pumping the hydraulic oil from the hydraulic cylinder into the expandable pad may further include pumping the hydraulic oil from the first hydraulic hose into the expandable pad.

In an exemplary embodiment, pumping the hydraulic oil from the hydraulic cylinder into the first hydraulic hose may include pumping the hydraulic oil from the hydraulic cylinder into the first hydraulic hose by triggering an outlet valve disposed between the hydraulic cylinder and the first hydraulic hose.

In an exemplary embodiment, pumping the hydraulic oil from the first hydraulic hose into the expandable pad may include aligning the horizontal thorough hole with the first opening and the second opening through pushing down the plunger rod.

In an exemplary embodiment, aligning the horizontal thorough hole with the first opening and the second opening through pushing down the plunger rod may include disposing the plunger head at an adjustable distance under the residual limb. In an exemplary embodiment, aligning the horizontal thorough hole with the first opening and the second opening through pushing down the plunger rod may further include tapping the plunger head by the residual limb through slipping down the residual limb inside the socket responsive to the volume decrease of the residual limb being more than the threshold. In an exemplary embodiment, the threshold may be in a range between 5% and 30% of an initial volume of the residual limb volume.

BRIEF DESCRIPTION OF THE DRAWINGS

The drawing figures depict one or more implementations in accord with the present teachings, by way of example

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Herein is disclosed an exemplary system for adjusting a prosthetic limb. The exemplary system provides stability and conformability for an amputee and also allows for volumetric changes in an amputee's residual limb. The exemplary prosthetic limb may have a socket that receives the residual limb of an amputee. Unlike traditional sockets for prosthetic limbs that have a rigid or semi-rigid interior surface that conforms to most or all of the outer circumference of the residual limb, the exemplary socket may have an expandable pad mounted on the interior surface of the exemplary socket. The volume of the expandable pad may be controlled by a hydraulic system. As the residual limb loses volume, the hydraulic system expands the expandable pad by pumping a hydraulic oil into the expandable pad.

Figure 1A:
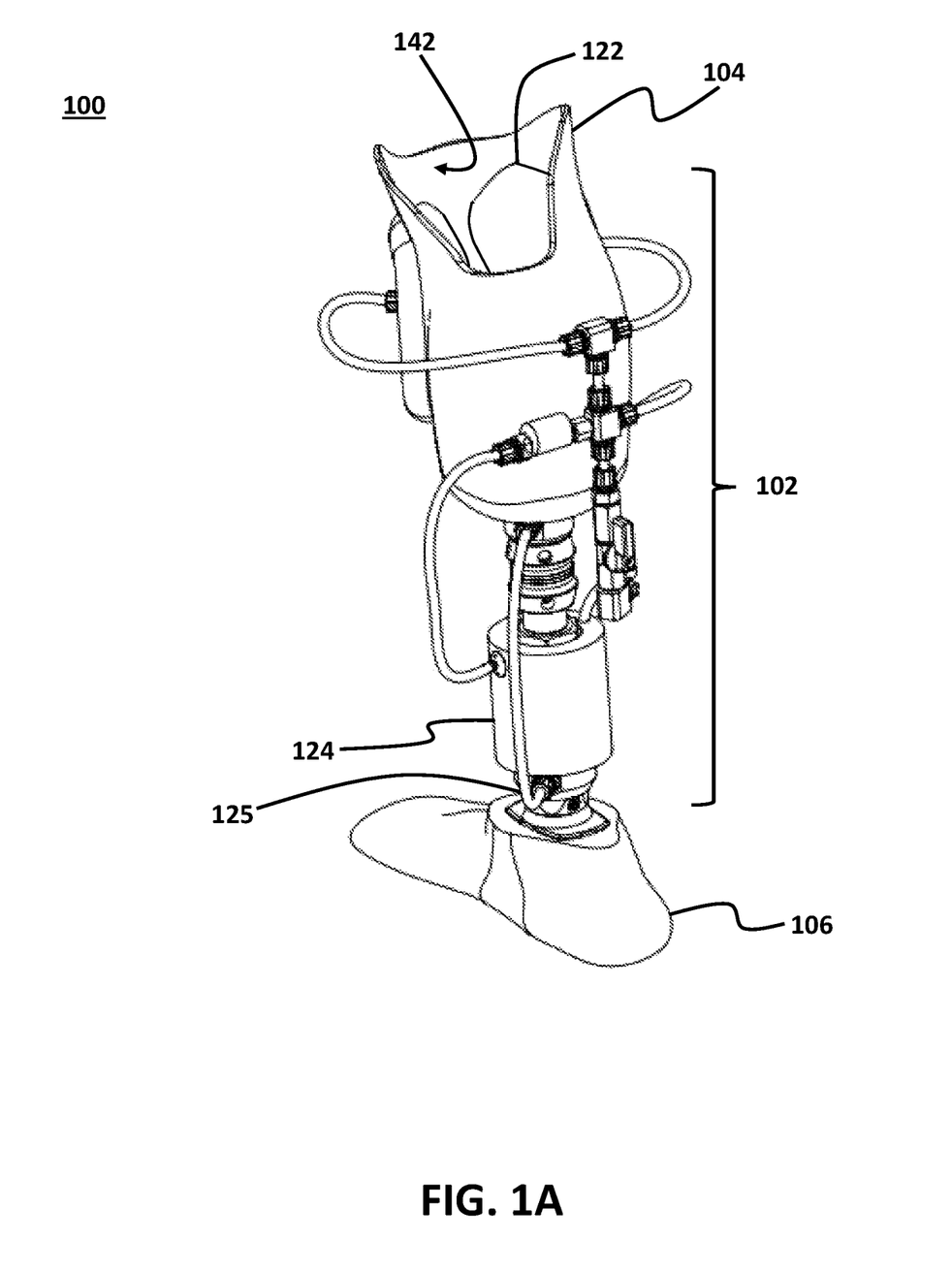
FIG. 1A illustrates a perspective view of an exemplary prosthetic limb, consistent with one or more exemplary embodiments of the present disclosure.
Figure 1B:
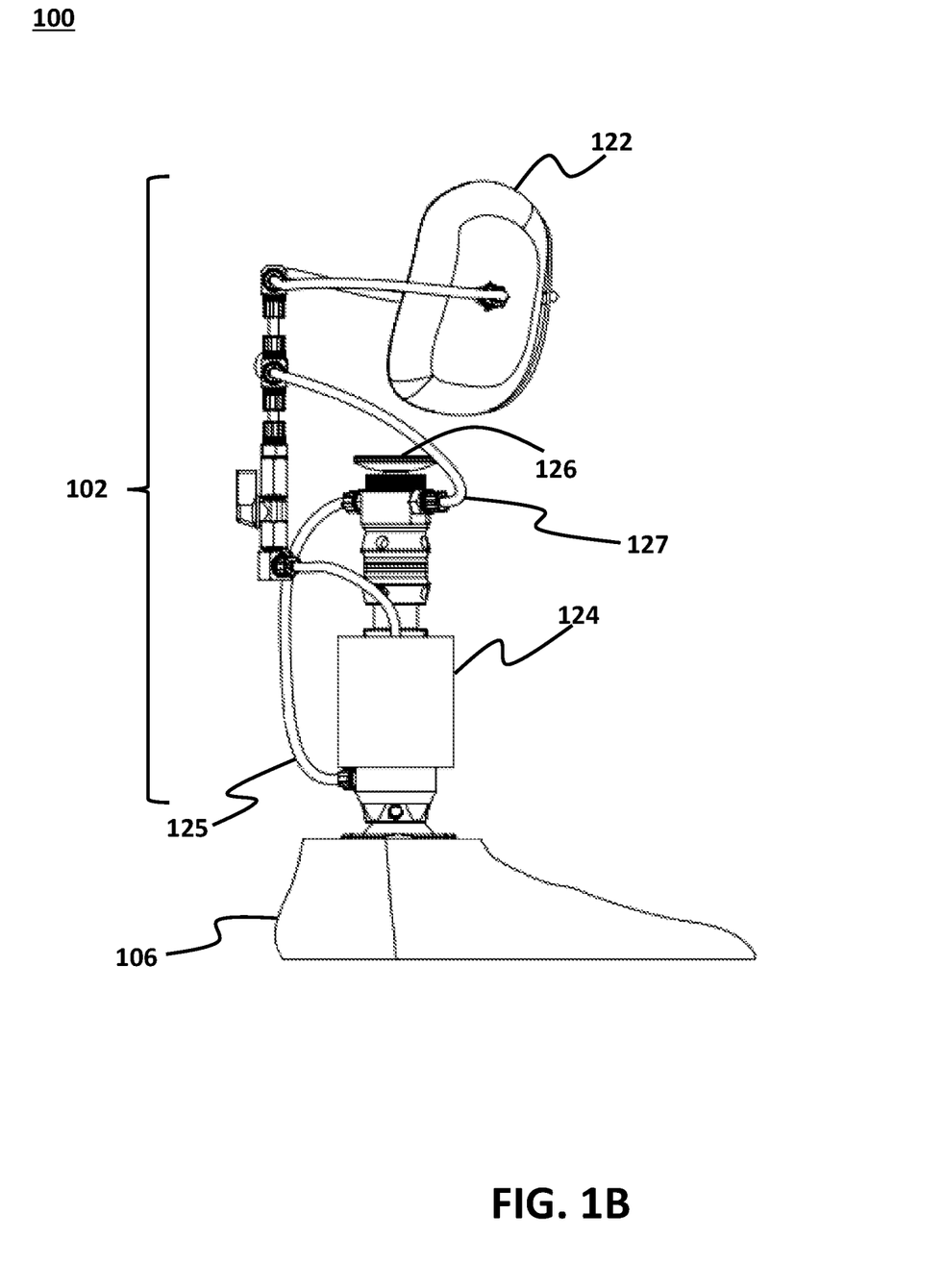
FIG. 1B illustrates a side view of an exemplary prosthetic limb, consistent with one or more exemplary embodiments of the present disclosure.

FIG. 1A shows a perspective view of an exemplary prosthetic limb 100, consistent with one or more exemplary embodiments of the present disclosure. FIG. 1B shows a side view of an exemplary prosthetic limb 100, consistent with one or more exemplary embodiments of the present disclosure. As shown in FIG. 1A and FIG. 1B, in an exemplary embodiment, prosthetic limb 100 may include a hydraulic system 102, a socket 104, and an artificial foot 106. In an exemplary embodiment, hydraulic system 102 may include an expandable pad 122, a hydraulic cylinder 124, and a plunger mechanism 126. In an exemplary embodiment, expandable pad 122 may be mounted onto an interior surface 142 of socket 104. In an exemplary embodiment, hydraulic cylinder 124 may be filled with hydraulic oil.

Figure 2A:
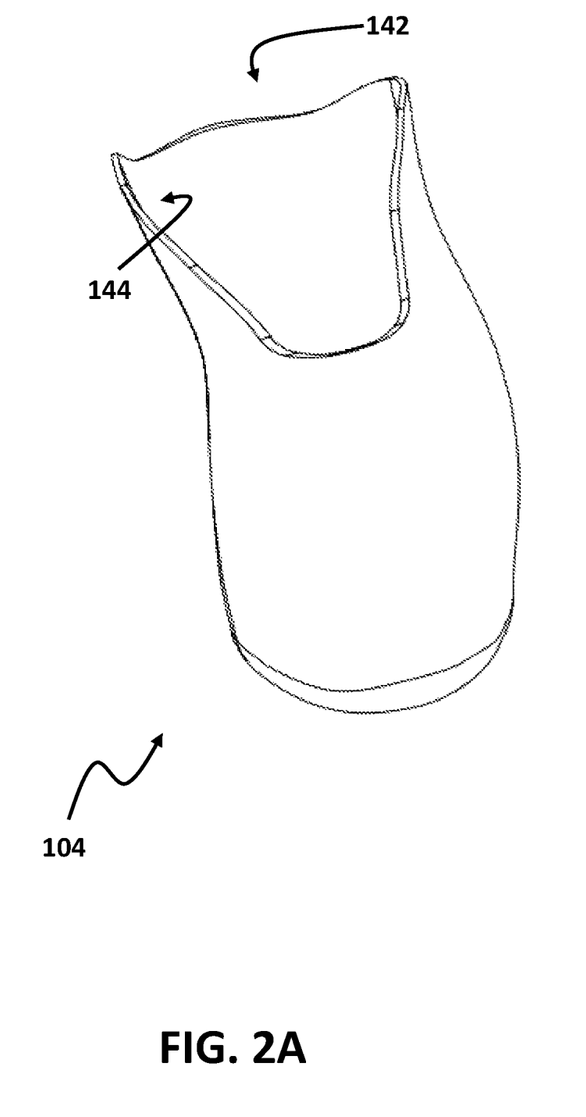
FIG. 2A illustrates a perspective view of an exemplary socket utilized in the prosthetic limb, consistent with one or more exemplary embodiments of the present disclosure.
Figure 2B:
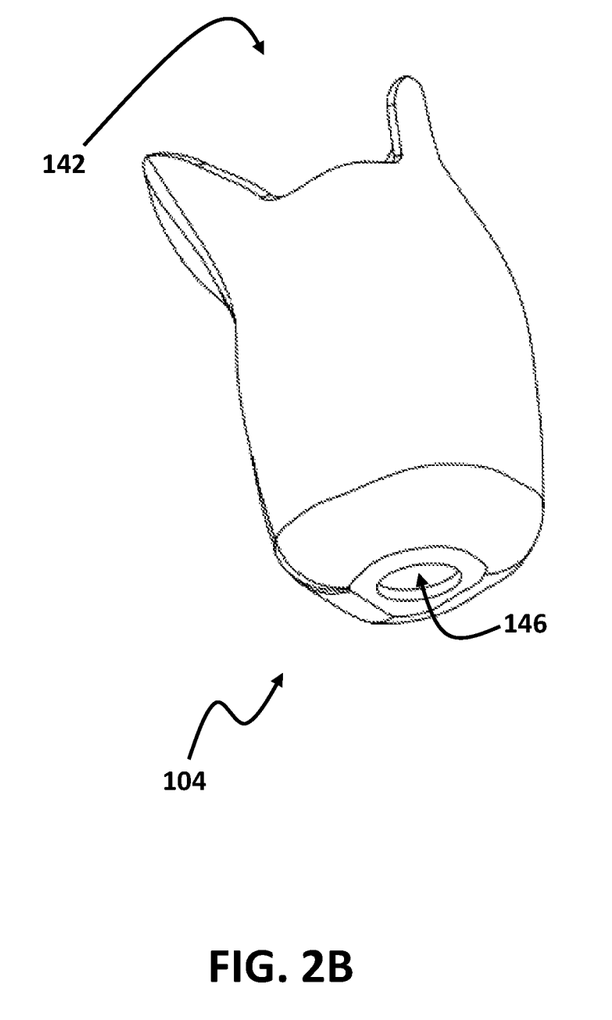
FIG. 2B illustrates a perspective view of an exemplary socket utilized in the prosthetic limb, consistent with one or more exemplary embodiments of the present disclosure.

FIG. 2A shows a perspective view of an exemplary socket 104 utilized in prosthetic limb 100, consistent with one or more exemplary embodiments of the present disclosure. FIG. 2B shows another perspective view of an exemplary socket 104 utilized in prosthetic limb 100, consistent with one or more exemplary embodiments of the present disclosure. As shown in FIG. 2A and FIG. 2B, in an exemplary embodiment, socket 104 may include a residual limb opening 142, a cup-shaped interior surface 144, and a brim 146. In an exemplary embodiment, residual limb opening 142 may be positioned at a top end of socket 104. In an exemplary embodiment, cup-shaped interior surface 144 may be shaped to receive the residual limb of an amputee.

In an exemplary embodiment, expandable pad 122 may be mounted onto cup-shaped interior surface 144 of socket 104. In an exemplary embodiment, expandable pad 122 may grip the residual limb of the amputee responsive to expandable pad 122 being expanded. In an exemplary embodiment, brim 146 may be positioned at bottom open end of socket 104. In an exemplary embodiment, cup-shaped interior surface 144 may allow the residual limb of the amputee to slip down inside socket 104 responsive to the volume decrease of the residual limb.

As shown in FIG. 1B, hydraulic system 102 may further include a first hydraulic hose 125 and a second hydraulic hose 127. In an exemplary embodiment, first hydraulic hose 125 may refer to a hose that is connected to hydraulic cylinder 124 and second hydraulic hose 127 may refer to a hose that is connected to expandable pad 122. In an exemplary embodiment, first hydraulic hose 125 and second hydraulic hose 127 may provide fluid communication between hydraulic cylinder 124 and expandable pad 104. As shown in FIG. 1B, in order to prevent fluid communication between hydraulic cylinder 124 and expandable pad 104, plunger mechanism 126 may be disposed between first hydraulic hose 125 and second hydraulic hose 127.

Figure 3:
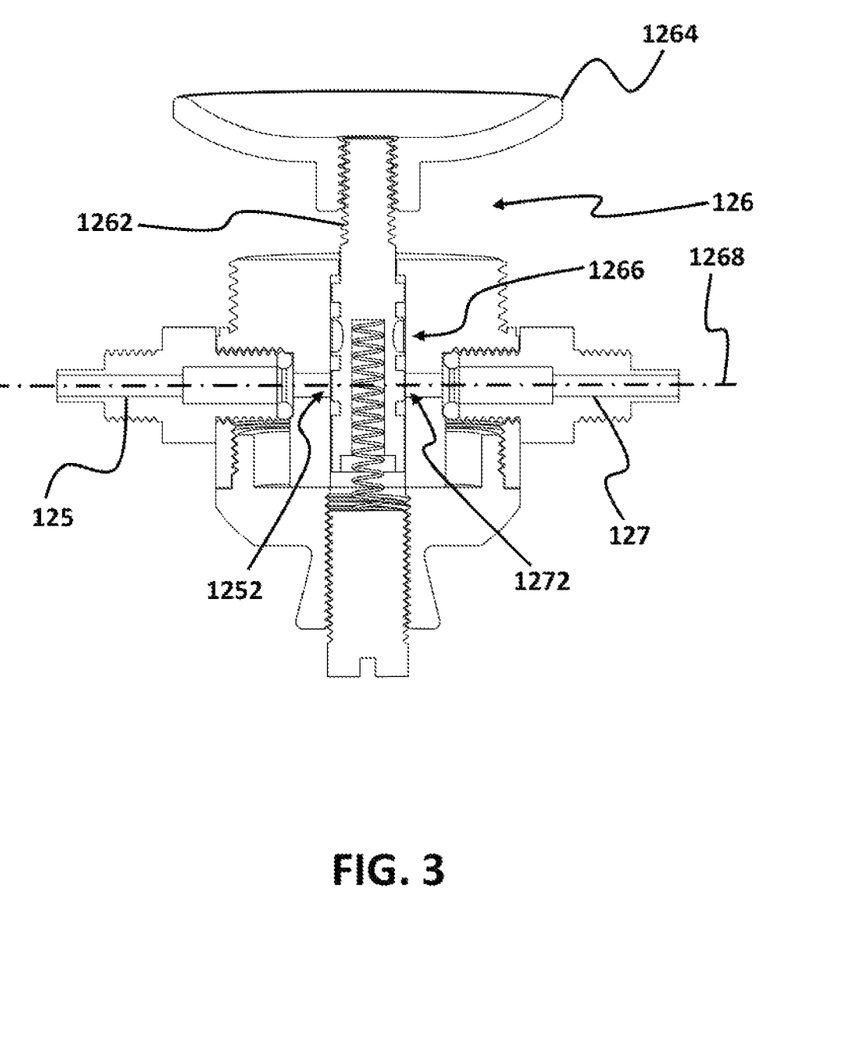
FIG. 3 illustrates an exemplary plunger mechanism utilized in the prosthetic limb, consistent with one or more exemplary embodiments of the present disclosure.

FIG. 3 shows plunger mechanism 126 utilized in prosthetic limb 100, consistent with one or more exemplary embodiments of the present disclosure. As shown in FIG. 3, plunger mechanism 126 may include a plunger rod 1262 and a plunger head 1264. In an exemplary embodiment, in order to prevent fluid communication between hydraulic cylinder 124 and expandable pad 104, plunger rod 1262 of plunger mechanism 126 may be disposed between first hydraulic hose 125 and second hydraulic hose 127. In an exemplary embodiment, plunger rod 1262 may include a horizontal thorough hole 1266. In an exemplary embodiment, horizontal thorough hole 1266 may refer to a hole that is provided along a diameter of plunger rod 1262 and is open at both end thereof. In an exemplary embodiment, horizontal thorough hole 1262 may provide a fluid communication between two opposite sides of plunger rod 1262. For example, in an exemplary embodiment, each end of horizontal thorough hole 1266 may be connected to a respective hose. and thereby may provide a fluid communication between these respective hoses. In an exemplary embodiment, plunger head 1264 may be mounted onto plunger rod 1262. In an exemplary embodiment, in response to plunger head 1264 being tapped, plunger mechanism 126 may allow fluid communication between first hydraulic hose 125 and second hydraulic hose 127.

As shown in FIG. 3, in an exemplary embodiment, first hydraulic hose 125 and second hydraulic hose 127 may be connected to opposite sides of plunger mechanism 126. In an exemplary embodiment, first hydraulic hose 125 may be connected to plunger mechanism 126 through a first opening 1252, and second hydraulic hose 127 may be connected to plunger mechanism 126 through a second opening 1272. In an exemplary embodiment, first opening 1252 and second opening 1272 may be provided along an axis 1268. In an exemplary embodiment, in response to plunger head 1264 being tapped, plunger head 1264 may push down plunger rod 1262 and thereby horizontal thorough hole 1266 may be placed in line with the axis 1268. In an exemplary embodiment, when horizontal thorough hole 1266 is placed in line with axis 1268, horizontal thorough hole 1266 may be aligned with first opening 1252 and second opening 1272 and, consequently, hydraulic oil may be pumped from first hydraulic hose 125 into second hydraulic hose 127. When first hydraulic hose 125 is in fluid communication with hydraulic cylinder 124 and second hydraulic hose is in fluid communication with expandable pad 104, in an exemplary embodiment, aligning horizontal thorough hole 1266 with first opening 1252 and second opening 1272 may provide fluid communication between hydraulic cylinder 124 and expandable pad 104. In an exemplary embodiment, pumping hydraulic oil from hydraulic cylinder 124 into expandable pad 104 may cause expandable pad 104 to be expanded.

Figure 4:
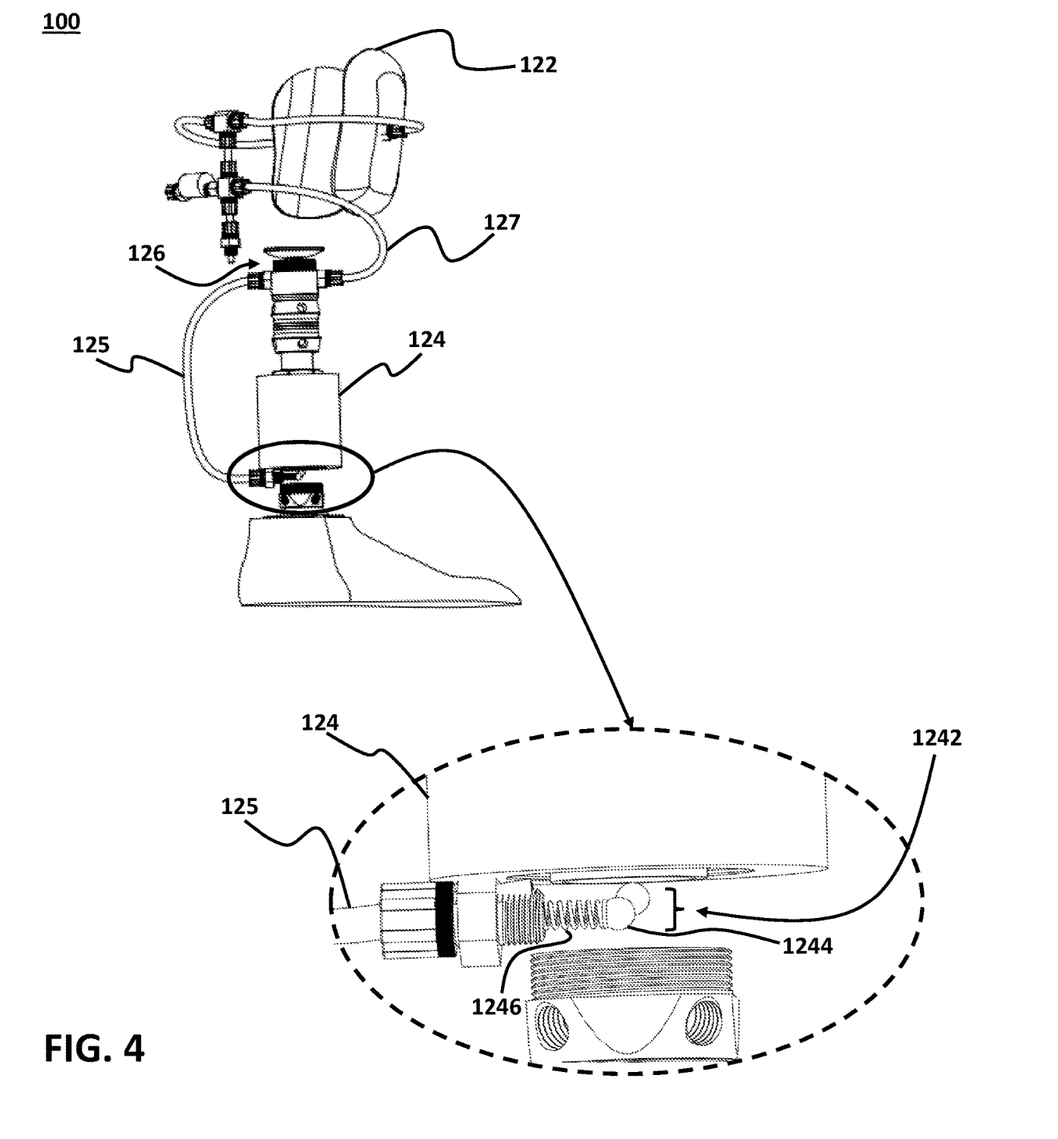
FIG. 4 illustrates a detailed view of an exemplary hydraulic cylinder, consistent with one or more exemplary embodiments of the present disclosure.

FIG. 4 shows a detailed view of hydraulic cylinder 124, consistent with one olr more exemplary embodiments of the present disclosure. As shown in FIG. 4, in an exemplary embodiment, hydraulic cylinder 124 may further include an outlet valve 1242. In an exemplary embodiment, outlet valve 1242 may be disposed between hydraulic cylinder 124 and first hydraulic hose 125. In an exemplary embodiment, in a response to outlet valve 1242 being triggered, outlet valve 1242 may allow fluid communication between hydraulic cylinder 124 and first hydraulic hose 125. In an exemplary embodiment, "trigger" may refer to any kind of external motivation that pushes a ball 1244 against a spring 1246 and thereby allow the hydraulic oil passes through outlet valve 1242. In an exemplary embodiment, due to the higher fluid pressure in hydraulic cylinder 124, in response to outlet valve 1242 being triggered, an amount of hydraulic oil may be pumped from hydraulic cylinder 124 into first hydraulic hose 125. In an exemplary embodiment, the amount of hydraulic oil that is pumped from hydraulic cylinder 124 into first hydraulic hose 125 may be adjusted by utilizing different kinds of valves as outlet valve 1242.

In an exemplary embodiment, outlet valve 1242 may be connected to socket 104. In an exemplary embodiment, outlet valve 1242 may be disposed under socket 104. In an exemplary embodiment, socket 104 may trigger outlet valve 1242 responsive to socket 104 being pushed by residual limb. In an exemplary embodiment, in response to amputee's walking, residual limb may push down socket 104 and, thereby, socket 104 may trigger outlet valve 1242.

In an exemplary embodiment, responsive to amputee's taking a step, a force may be applied to socket 104 from residual limb of the amputee. In an exemplary embodiment, the force applied from residual limb of amputee to socket 104 may be a downward force that may push down socket 104 to trigger outlet valve 1242 and thereby an amount of hydraulic oil may be pumped from hydraulic cylinder 124 into first hydraulic hose 125. In an exemplary embodiment, after a number of steps taken by the amputee, first hydraulic hose 125 may be filled with hydraulic oil pumped into first hydraulic hose 125 from hydraulic cylinder 124.

As shown in FIG. 2, in an exemplary embodiment, cup-shaped interior surface 144 of socket 104 may be manufactured based on a residual limb's shape. According to the fact that the residual limb probably have a substantially conical shape that has smaller diameters in bottom section of the residual limb and has larger diameters in top section of the residual limb, cup-shaped interior surface 144 may have a substantially conical shape. In an exemplary embodiment, substantially conical shape of cup-shaped interior surface 144 may allow the residual limb of the amputee to slip down inside socket 104, responsive to a volume decrease of the residual limb due to the amputee taking steps.

Figure 5:
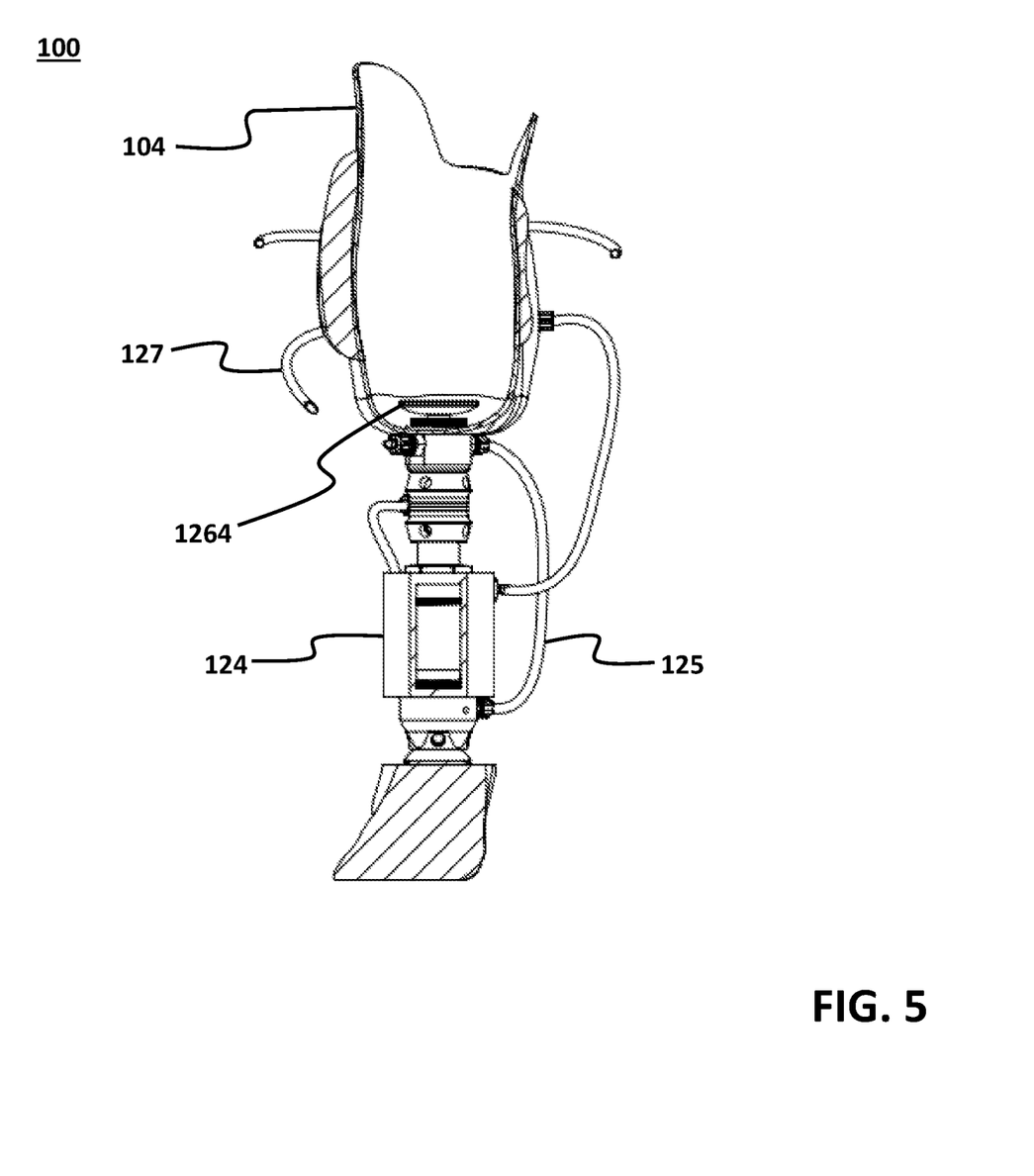
FIG. 5 illustrates a section-view of an exemplary prosthetic limb, consistent with one or more exemplary embodiments of the present disclosure.

FIG. 5 shows a section-view of prosthetic limb 100, consistent with one or more exemplary embodiments of the present disclosure. As shown in FIG. 5, plunger head 1264 may be disposed in a bottom section of socket 104. In an exemplary embodiment, it may be understood that brim 146 may provide significant benefits including, but not limited to, allowing plunger head 1264 to be disposed inside socket 104. In an exemplary embodiment, plunger head 1264 may be positioned at an adjustable distance above brim 146 and inside socket 104. In an exemplary embodiment, the adjustable distance may determine the distance between plunger head 1264 and normal residual limb (without volume decrease). In an exemplary embodiment, the sensitivity of hydraulic system 102 may be adjusted by altering the distance between plunger head 1264 and normal residual limb (without volume decrease). In an exemplary embodiment, the sensitivity of hydraulic system 102 may refer to the amount of the volume decrease of the residual limb that urges hydraulic system 102 to be activated and to expand expandable pad 122.

In an exemplary embodiment, due to volume decrease of the amputee's residual limb, the residual limb may slip down inside socket 104. In an exemplary embodiment, responsive to slipping down of the residual limb inside socket 104, the residual limb may tap plunger head 1264. In an exemplary embodiment, responsive to plunger head 1264 being tapped, plunger rod 1262 may be pushed down. In an exemplary embodiment, responsive to plunger rod 1262 being pushed down, horizontal thorough hole 1266 may be aligned with first hydraulic hose 125 and second hydraulic hose 127. In an exemplary embodiment, responsive to horizontal thorough hole 1266 being aligned with first opening 1252 and second opening 1272, an amount of hydraulic oil may be pumped from first hydraulic hose 125 to second hydraulic hose 127 horizontal thorough hole 1266.

As mentioned above, in an exemplary embodiment, responsive to volume decrease of the residual limb of the amputee, the residual limb may slip down inside socket 104. In an exemplary embodiment, responsive to slipping down of the residual limb inside socket 104, the residual limb may tap plunger head 1264 when the amputee takes a step. In an exemplary embodiment, after a number of steps taken by the amputee, for example 10 to 20 steps, second hydraulic hose 127 may be filled with hydraulic oil pumped into second hydraulic hose 127 from first hydraulic hose 125. In an exemplary embodiment, the number of steps that is enough for second hydraulic hose 127 to be filled with hydraulic oil may be adjusted by altering some parameters of prosthetic limb 100. For example, by altering diameter or length of first hydraulic hose 125 and second hydraulic hose 127, the number of steps that is enough for second hydraulic hose 127 to be filled with hydraulic oil may be changed. In an exemplary embodiment, responsive to hydraulic oil being pumped into second hydraulic hose 127 from first hydraulic hose 125, hydraulic oil may be pumped into expandable pad 122.

In an exemplary embodiment, the pumped oil into expandable pad 122 may expand expandable pad 122. In an exemplary embodiment, responsive to the residual limb being gripped by expandable pad 122, the residual limb may be pushed up due to the substantially conical shape of the residual limb. In an exemplary embodiment, expansion of expandable pad 122 may be continued until the residual limb is positioned at a distance from plunger head that prevents the residual limb from touching plunger head 1264 during an amputee's walking.

Figure 6:
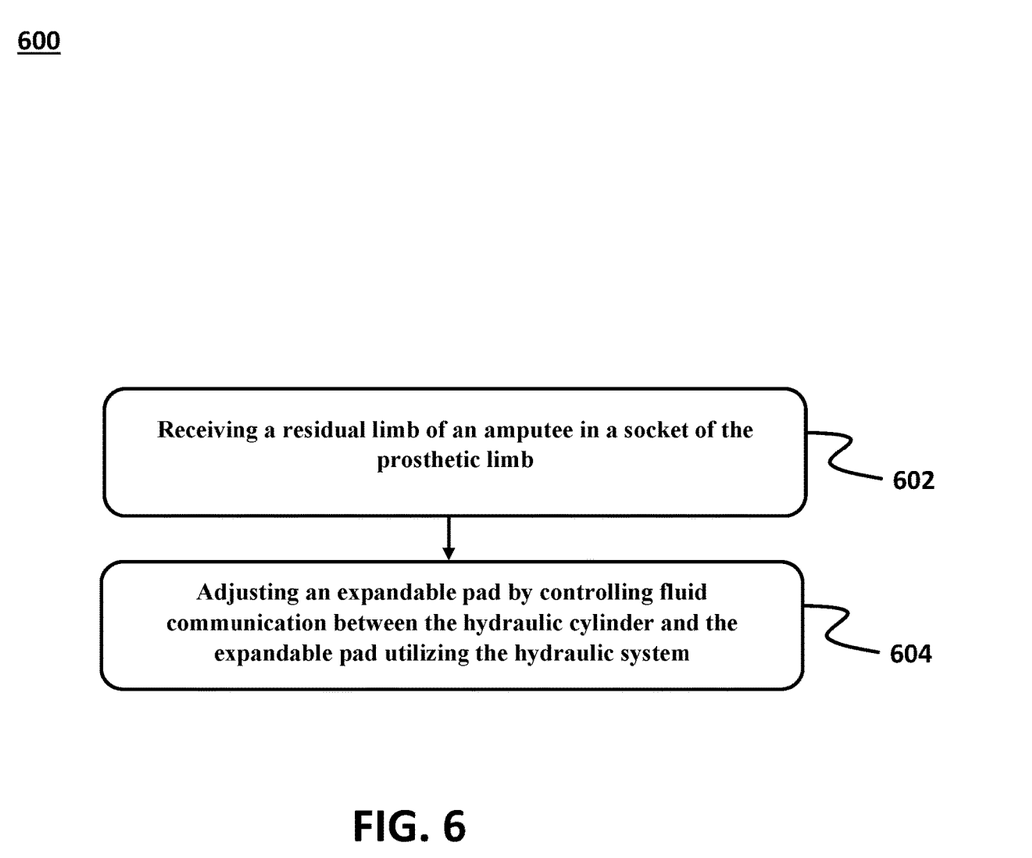
FIG. 6 illustrates a method for adjusting a prosthetic limb, consistent with one or more exemplary embodiments of the present disclosure.

FIG. 6 illustrates a method 600 for adjusting a prosthetic limb, consistent with one or more exemplary embodiments of the present disclosure. In an exemplary embodiment, method 600 may be utilized for adjusting a prosthetic limb similar to prosthetic limb 100 of FIG. 1.

Referring to FIGS. 1 and 6, in an exemplary embodiment, method 600 may include a step 602 of receiving a residual limb of an amputee in socket 104 of prosthetic limb 100. As shown in FIG. 1, in an exemplary embodiment, prosthetic limb 100 may include a hydraulic system 102. In an exemplary embodiment, hydraulic system 102 may include an expandable pad 122 mounted onto an interior surface of socket 104 of prosthetic limb 100. In an exemplary embodiment, hydraulic system 102 may further include a hydraulic cylinder 124 filled with hydraulic oil and a plunger mechanism 126 disposed between hydraulic cylinder 124 and expandable pad 104.

With the further reference to FIG. 6, in an exemplary embodiment, method 600 may further include a step 604 of adjusting expandable pad 122 by controlling fluid communication between hydraulic cylinder 124 and expandable pad 104 utilizing hydraulic system 102. In an exemplary embodiment, adjusting expandable pad 104 by controlling fluid communication between hydraulic cylinder 124 and expandable pad 104 may include expanding expandable pad 104 by pumping the hydraulic oil from hydraulic cylinder 124 into expandable pad 104 responsive to an amount of volume decrease of the residual limb being more than a threshold. In an exemplary embodiment, the threshold may be adjusted by altering different parameters of the prosthetic limb. For example, the threshold may be adjusted by increasing or decreasing the adjustable distance. In an exemplary embodiment, the threshold may be in a range between 5% and 30% of an initial volume of the residual limb.

In an exemplary embodiment, pumping the hydraulic oil from hydraulic cylinder 124 into expandable pad 104 may include allowing fluid communication between hydraulic cylinder 124 and expandable pad 104 responsive to the volume decrease of the residual limb being equal to or more than the threshold. In an exemplary embodiment, hydraulic cylinder 124 may be associated with a hydraulic piston. In an exemplary embodiment, the hydraulic piston may pump the hydraulic oil out of hydraulic cylinder 124 by linear moving inside hydraulic cylinder 124.

In an exemplary embodiment, allowing fluid communication between hydraulic cylinder 124 and expandable pad 104 may include allowing fluid communication between hydraulic cylinder 124 and expandable pad 104 utilizing plunger mechanism 126. As shown in FIG. 3, in an exemplary embodiment, plunger mechanism 126 may include a plunger rod 1262 disposed between hydraulic cylinder 124 and expandable pad 104. In an exemplary embodiment, plunger rod 1262 may be connected to hydraulic cylinder 124 through a first hydraulic hose 125. In an exemplary embodiment, plunger rod 1262 may also be connected to expandable pad 104 through a second hydraulic hose 127. In an exemplary embodiment, plunger rod 1262 may further include a horizontal thorough hole 1266 provided along a dimeter of plunger rod 1262 and is open at both ends thereof. In an exemplary embodiment, thorough hole may refer to a hole that is open at both end of the hole. In an exemplary embodiment, plunger mechanism 126 may further include a plunger head 1264 mounted onto plunger rod 1262.

As shown in FIG. 3, in an exemplary embodiment, first hydraulic hose 125 may be connected to plunger rod 1262 through a first opening 1252. Similarly, in an exemplary embodiment, second hydraulic hose 127 may be connected to plunger rod 1262 through a second opening 1272. In an exemplary embodiment, first opening 1252 and second opening 1272 may be provided in front of each other. In an exemplary embodiment, allowing fluid communication between hydraulic cylinder 124 and expandable pad 104 may include aligning horizontal thorough hole 1266 with first opening 1252 and second opening 1272 through pushing down plunger rod 1262. As shown in FIG. 3, in an exemplary embodiment, plunger rod 1262 may be pushed down until horizontal thorough hole 1266 is aligned with axis 1268, then, the fluid communication may be allowed between hydraulic cylinder 124 and expandable pad 104.

In an exemplary embodiment, expanding expandable pad 104 by pumping the hydraulic oil from hydraulic cylinder 124 into expandable pad 104 may include filling first hydraulic hose 125 with the hydraulic oil by pumping the hydraulic oil from hydraulic cylinder 124 into second hydraulic hose 127. In an exemplary embodiment, expanding expandable pad 104 by pumping the hydraulic oil from hydraulic cylinder 124 into expandable pad 104 may further include pumping the hydraulic oil from first hydraulic hose 125 into expandable pad 104. In an exemplary embodiment, it may be understood that when first hydraulic hose 125 is filled with hydraulic oil, pumping hydraulic oil from hydraulic cylinder 124 may cause pumping hydraulic oil into second hydraulic hose 127 from first hydraulic hose 125.

In an exemplary embodiment, pumping the hydraulic oil from hydraulic cylinder 124 into first hydraulic hose 125 may include pumping the hydraulic oil from hydraulic cylinder 124 into first hydraulic hose 125 by triggering an outlet valve 1242 disposed between hydraulic cylinder 124 and first hydraulic hose 125. In an exemplary embodiment, triggering outlet valve 1242 may include triggering outlet valve 1242 by tapping a ball 1244 of outlet valve 1242 utilizing hydraulic cylinder 124 responsive to the amputee taking step.

Figure 7:
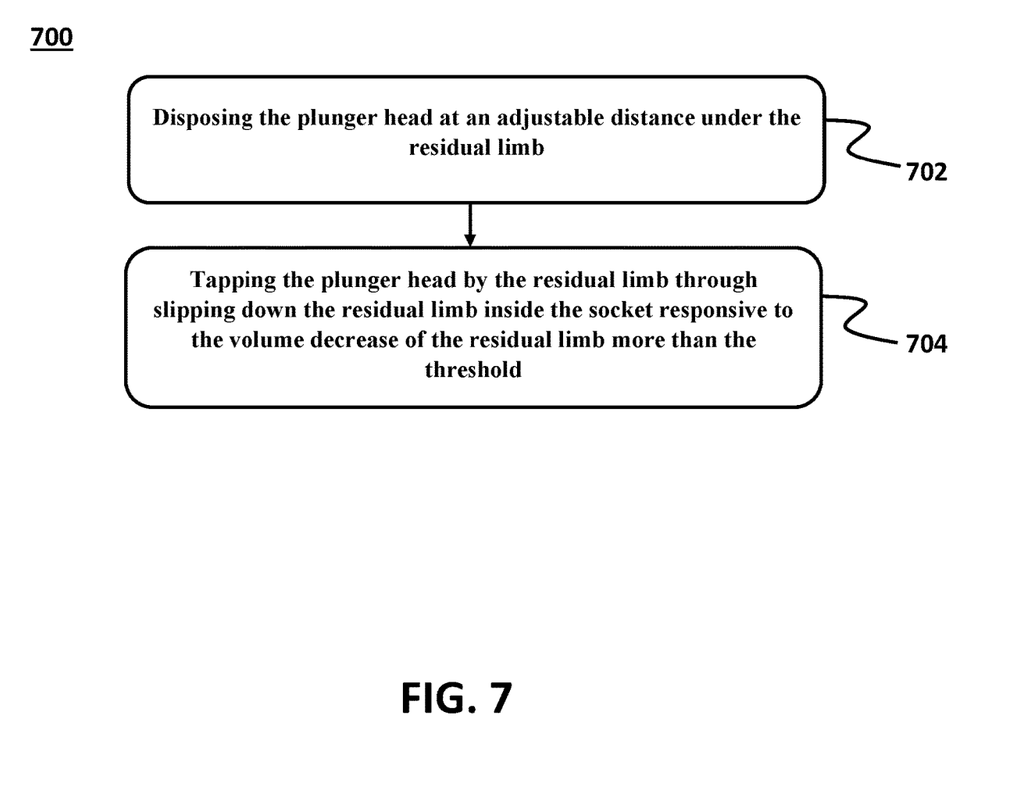
FIG. 7 illustrates a method for aligning the horizontal thorough hole with the first opening and the second opening through pushing down the plunger rod, consistent with one or more exemplary embodiments.

In an exemplary embodiment, pumping the hydraulic oil from first hydraulic hose 125 into expandable pad 104 may include aligning horizontal through hole 1266 with first opening 1252 and second opening 1272 through pushing down plunger rod 1262. FIG. 7 shows an exemplary method 700 for aligning horizontal through hole 1266 with first opening 1252 and second opening 1272. As shown in FIG. 7, in an exemplary embodiment, aligning horizontal through hole 1266 with first opening 1252 and second opening 1272 through pushing down plunger rod 1262 may include a step 702 of disposing plunger head 1264 at an adjustable distance under the residual limb. In an exemplary embodiment, aligning horizontal through hole 1266 with first opening 1252 and second opening 1272 through pushing down plunger rod 1262 may further include a step 704 of tapping plunger head 1262 by the residual limb through slipping down the residual limb inside socket 104 responsive to the volume decrease of the residual limb being more than the threshold. In an exemplary embodiment, the threshold may be adjusted by altering different parameters of the prosthetic limb. For example, the threshold may be adjusted by increasing or decreasing the adjustable distance. In an exemplary embodiment, the threshold may be in a range between 5% and 30% of an initial volume of the residual limb. In an exemplary embodiment, responsive to volume decrease of the residual limb of the amputee, the residual limb may slip down inside socket 104. In an exemplary embodiment, responsive to slipping down of the residual limb inside socket 104, the residual limb may tap plunger head 1264 when the amputee takes a step and thereby align horizontal through hole 1266 with first opening 1252 and second opening 1272 and thereby allow fluid communication between first hydraulic hose 125 and expandable pad 104.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A hydraulic system for adjusting a prosthetic limb, the hydraulic system comprising:
   an expandable pad mounted onto an interior surface of a socket of the prosthetic limb, the socket configured to receive a residual limb of an amputee;
   a hydraulic cylinder filled with hydraulic oil; and
   a plunger mechanism disposed between the hydraulic cylinder and the expandable pad, the plunger mechanism configured to:
      control fluid communication between the hydraulic cylinder and the expandable pad;
      prevent fluid communication between the hydraulic cylinder and the expandable pad responsive to the amount of the volume decrease of the residual limb being less than the threshold; and
      allow fluid communication between the hydraulic cylinder and the expandable pad responsive to the amount of the volume decrease of the residual limb being equal to or more than the threshold, wherein the hydraulic system is configured to expand the expandable pad by pumping the hydraulic oil from the hydraulic cylinder into the expandable pad responsive to an amount of a volume decrease of the residual limb being more than a threshold.

2. The hydraulic system of claim 1, wherein the hydraulic system further comprises:
a first hydraulic hose configured to provide fluid communication between the plunger mechanism and the hydraulic cylinder; and
a second hydraulic hose configured to provide fluid communication between the plunger mechanism and the expandable pad.

3. The hydraulic system of claim 2, wherein the plunger mechanism comprises:
a plunger rod disposed between the first hydraulic hose and the second hydraulic hose, the plunger rod configured to prevent fluid communication between the hydraulic cylinder and the expandable pad, the plunger rod comprising a horizontal thorough hole; and
a plunger head mounted onto the plunger rod;
wherein the plunger mechanism is configured to allow fluid communication between the hydraulic cylinder and the expandable pad by aligning the horizontal thorough hole with the first hydraulic hose and the second hydraulic hose responsive to the plunger head being tapped.

4. The hydraulic system of claim 3, wherein the hydraulic cylinder further comprises an outlet valve disposed between the hydraulic cylinder and the first hydraulic hose, the outlet valve configured to allow fluid communication between the hydraulic cylinder and the first hydraulic hose responsive to the outlet valve being triggered.

5. The hydraulic system of claim 4, wherein the outlet valve is connected to the socket, the socket configured to trigger the outlet valve responsive to the socket pushed by the residual limb.

6. The hydraulic system of claim 5, wherein the socket comprises:
a residual limb opening at a top end of the socket;
a cup-shaped interior surface shaped to receive the residual limb of the amputee, the expandable pad mounted onto the cup-shaped interior surface of the socket, the expandable pad configured to grip the residual limb responsive to the expandable pad being expanded; and
a brim defining a bottom open end, the plunger head positioned in an adjustable distance above the brim and inside the socket.

7. The hydraulic system of claim 6, wherein:
the cup-shaped interior surface is configured to allow the residual limb to slip down inside the socket responsive to the volume decrease of the residual limb more than the threshold, and
the plunger head is configured to be tapped by the slipped residual limb.

8. The hydraulic system of claim 7, wherein the threshold is in a range between 5% and 30% of an initial volume of the residual limb.

9. A method for adjusting a prosthetic limb, the method comprising:
receiving a residual limb of an amputee in a socket of the prosthetic limb, the prosthetic limb comprising a hydraulic system comprising:
an expandable pad mounted onto an interior surface of the socket of the prosthetic limb;
a hydraulic cylinder filled with hydraulic oil; and
a plunger mechanism disposed between the hydraulic cylinder and the expandable pad; and
adjusting the expandable pad by controlling fluid communication between the hydraulic cylinder and the expandable pad utilizing the hydraulic system;
wherein:
adjusting the expandable pad by controlling fluid communication between the hydraulic cylinder and the expandable pad comprises expanding the expandable pad by pumping the hydraulic oil from the hydraulic cylinder into the expandable pad responsive to an amount of volume decrease of the residual limb being more than a threshold;
pumping the hydraulic oil from the hydraulic cylinder into the expandable pad comprises allowing fluid communication between the hydraulic cylinder and the expandable pad responsive to the volume decrease of the residual limb being equal to or more than the threshold; and
allowing fluid communication between the hydraulic cylinder and the expandable pad comprises allowing fluid communication between the hydraulic cylinder and the expandable pad utilizing a plunger mechanism, the plunger mechanism comprising:
a plunger rod disposed between the hydraulic cylinder and the expandable pad, the plunger rod connected to the hydraulic cylinder through a first hydraulic hose and connected to the expandable pad through a second hydraulic hose, the plunger rod comprising a horizontal thorough hole provided along a diameter of the plunger rod; and
a plunger head mounted onto the plunge rod.

10. The method of claim 9, wherein:
the first hydraulic hose is connected to the plunger rod through a first opening; and
the second hydraulic hose is connected to the plunger rod through a second opening, the second opening faced and aligned with the first opening.

11. The method of claim 10, wherein allowing fluid communication between the hydraulic cylinder and the expandable pad comprises aligning the horizontal thorough hole with the first opening and the second opening through pushing down the plunger rod.

12. The method of claim 11, wherein expanding the expandable pad by pumping the hydraulic oil from the hydraulic cylinder into the expandable pad comprises:
Filling the first hydraulic hose with the hydraulic oil by pumping the hydraulic oil from the hydraulic cylinder into the first hydraulic hose; and
pumping the hydraulic oil from the first hydraulic hose into the expandable pad.

13. The method of claim 12, wherein pumping the hydraulic oil from the hydraulic cylinder into the first hydraulic hose comprises pumping the hydraulic oil from the hydraulic cylinder into the first hydraulic hose by triggering an outlet valve disposed between the hydraulic cylinder and the first hydraulic hose.

14. The method of claim 13, wherein triggering the outlet valve comprises triggering the outlet valve by tapping a ball of the outlet valve utilizing the hydraulic cylinder responsive to the amputee taking step.

15. The method of claim 14, wherein pumping the hydraulic oil from the first hydraulic hose into the expandable pad comprises aligning the horizontal thorough hole with the first opening and the second opening through pushing down the plunger rod comprising:

disposing the plunger head at an adjustable distance under the residual limb; and tapping the plunger head by the residual limb through slipping down the residual limb inside the socket responsive to the volume decrease of the residual limb being more than the threshold.

16. The method of claim 15, wherein the threshold is in a range between 5% and 30% of an initial volume of the residual limb.

* * * * *